(12) United States Patent
Thompson et al.

(10) Patent No.: US 9,717,572 B2
(45) Date of Patent: Aug. 1, 2017

(54) SYSTEM AND PROCESS FOR DUPLICATION OF DENTURES (75) Inventors: Timothy C. Thompson, Fountain Hills, AZ (US); Scott C. Keating, Louisville, CO (US); Andrzej J. Jakson, Amherst, NY (US)

(73) Assignee: GLOBAL DENTAL SCIENCE, LLC, Scottsdale, AZ (US)

( * ) Notice: Subject to any disclaimer, the term of this patent is extended or adjusted under 35 U.S.C. 154(b) by 0 days.

(21) Appl. No.: 13/823,466

(22) PCT Filed: Nov. 3, 2011

(86) PCT No.: PCT/US2011/059239
§ 371 (c)(1),
(2), (4) Date: Mar. 14, 2013

(87) PCT Pub. No.: WO2012/061659
PCT Pub. Date: May 10, 2012

(65) Prior Publication Data
US 2013/0209962 A1  Aug. 15, 2013

(51) Int. Cl.
A61C 13/00 (2006.01)
A61C 13/01 (2006.01)
(Continued)

(52) U.S. Cl.
CPC ........ *A61C 13/0004* (2013.01); *A61C 9/0006* (2013.01); *A61C 13/0009* (2013.01);
(Continued)

(58) Field of Classification Search
CPC ......... A61C 8/00; A61C 9/004; A61C 9/0046; A61C 13/0001; A61C 13/0004;
(Continued)

(56) References Cited

U.S. PATENT DOCUMENTS 200,445 A    2/1878  Fahnestock
321,847 A    7/1885  Peirce et al.
(Continued)

FOREIGN PATENT DOCUMENTS

CA    2505892      5/2004
JP    2008307281   12/2008
(Continued)

OTHER PUBLICATIONS

USPTO; Office Action dated Sep. 24, 2013 in U.S. Appl. No. 13/249,210.
(Continued)

*Primary Examiner* — Edward Moran
(74) *Attorney, Agent, or Firm* — Harvey Law, P.C.; Derrick Harvey (57) ABSTRACT

Systems and processes for the duplication of dentures from existing dentures. The interior and exterior of the dentures are scanned and a best fit procedure is used to create a fully digitized denture. The denture teeth are selected from a library that is the closest fit to the original denture teeth. The library teeth are offset a preset distance to compensate for the best fit. The teeth are then subtracted from the digitized denture. The margins of the denture are then cleaned after subtracting the teeth. The denture base is then ready for manufacturing. The teeth are then installed onto the denture base and provided to the patient.

17 Claims, 7 Drawing Sheets (51) Int. Cl.
*A61C 13/10* (2006.01)
*A61C 13/271* (2006.01)
*A61C 9/00* (2006.01)
*G06F 17/50* (2006.01)
*A61C 13/34* (2006.01)

(52) U.S. Cl.
CPC .............. *A61C 13/01* (2013.01); *A61C 13/10* (2013.01); *A61C 13/26* (2013.01); *G06F 17/50* (2013.01); *A61C 13/34* (2013.01)

(58) Field of Classification Search
CPC ............ A61C 13/0006; A61C 13/0009; A61C 13/0024; A61C 13/0027; A61C 13/01; A61C 13/08; A61C 13/10; A61C 13/1003; A61C 13/1013; A61C 13/34
USPC ........ 433/34, 37, 167, 168.1, 171, 172, 191, 433/192, 199.1, 200.1, 202.1, 213, 214, 433/215; 264/16–19
See application file for complete search history.

(56) References Cited

U.S. PATENT DOCUMENTS

| | | |
|---|---|---|
| 711,324 A | 10/1902 | Lacy |
| 1,223,450 A | 4/1917 | Van Allen |
| 1,293,627 A | 2/1919 | Bowers |
| 1,585,348 A | 5/1926 | Hick et al. |
| 1,652,910 A | 12/1927 | Psayla |
| 1,714,185 A | 5/1929 | Hugh |
| 1,863,591 A | 6/1932 | Crowell |
| 1,914,606 A | 6/1933 | Kinna et al. |
| 2,107,181 A | 2/1938 | Guyton |
| 2,418,833 A | 4/1947 | Harris et al. |
| 2,472,492 A | 6/1949 | Saffir |
| 2,641,835 A | 6/1953 | Greenmun |
| 2,985,961 A | 5/1961 | Schwartz |
| 2,994,957 A | 8/1961 | Mcleod |
| 3,083,459 A | 4/1963 | McMurry et al. |
| 3,241,238 A | 3/1966 | Kertsten |
| 3,644,996 A | 2/1972 | Weinkle |
| 3,667,123 A | 6/1972 | Huey |
| 3,727,309 A | 4/1973 | Huey |
| 3,748,739 A | 7/1973 | Thibert |
| 3,813,777 A | 6/1974 | Van Handel et al. |
| 3,844,702 A | 10/1974 | Dimmer et al. |
| 4,029,632 A | 6/1977 | Gross et al. |
| 4,227,877 A | 10/1980 | Tureaud et al. |
| 4,247,287 A | 1/1981 | Gigante |
| 4,299,573 A | 11/1981 | Ricci |
| 4,533,325 A | 8/1985 | Blair |
| 4,591,341 A | 5/1986 | Andrews |
| 4,634,377 A | 1/1987 | Behrend |
| 4,784,608 A | 11/1988 | Mays |
| 4,931,016 A | 6/1990 | Sillard |
| 5,098,296 A | 3/1992 | Cullen |
| 5,151,044 A | 9/1992 | Rotsaert |
| 5,188,529 A | 2/1993 | Luth |
| 5,427,906 A | 6/1995 | Hansen |
| 5,672,305 A | 9/1997 | Kogure |
| 5,711,668 A | 1/1998 | Huestis |
| 5,716,214 A | 2/1998 | Lund |
| 5,718,584 A | 2/1998 | Wong |
| 5,833,461 A | 11/1998 | Wong |
| 5,839,900 A | 11/1998 | Billet et al. |
| 6,056,547 A | 5/2000 | Names |
| 6,139,322 A | 10/2000 | Liu |
| 6,149,427 A | 11/2000 | Van Handel |
| 6,224,372 B1 * | 5/2001 | Ibsen et al. ................. 433/168.1 |
| 6,227,851 B1 | 5/2001 | Chishti |
| 6,384,107 B2 | 5/2002 | Liu |
| 6,422,864 B1 | 7/2002 | Glatt |
| 6,488,503 B1 * | 12/2002 | Lichkus et al. ............ 433/202.1 |
| 6,616,444 B2 | 9/2003 | Andreiko et al. |
| 6,851,949 B1 | 2/2005 | Sachdeva |
| 7,021,934 B2 | 4/2006 | Aravena |
| 7,153,135 B1 | 12/2006 | Thomas |
| 7,234,940 B2 | 6/2007 | Weissman |
| 7,433,810 B2 | 10/2008 | Pavloskaia et al. |
| 7,474,932 B2 * | 1/2009 | Geng .............................. 700/98 |
| 7,758,345 B1 | 7/2010 | Christensen |
| 8,043,091 B2 | 10/2011 | Schmitt |
| 8,348,669 B1 | 1/2013 | Schmitt |
| 8,567,408 B2 | 10/2013 | Roettger |
| 8,641,938 B2 | 2/2014 | Howe |
| 8,801,431 B2 | 8/2014 | Thompson et al. |
| 8,875,398 B2 | 11/2014 | Balshi et al. |
| 9,055,993 B2 | 6/2015 | Grobbee et al. |
| 2002/0015934 A1 | 2/2002 | Rubbert et al. |
| 2002/0180760 A1 | 12/2002 | Rubbert et al. |
| 2003/0108845 A1 | 6/2003 | Giovannone |
| 2003/0162147 A1 | 8/2003 | Dequeker |
| 2003/0163291 A1 | 8/2003 | Jordan et al. |
| 2003/0211444 A1 | 11/2003 | Andrews |
| 2004/0005530 A1 | 1/2004 | Mullaly |
| 2004/0029068 A1 | 2/2004 | Sachdeva et al. |
| 2004/0219490 A1 * | 11/2004 | Gartner et al. ................ 433/218 |
| 2005/0175957 A1 | 8/2005 | Haje |
| 2005/0186539 A1 | 8/2005 | McLean et al. |
| 2005/0284489 A1 | 12/2005 | Ambis |
| 2006/0040232 A1 | 2/2006 | Shoup |
| 2006/0040236 A1 | 2/2006 | Schmitt |
| 2006/0063135 A1 | 3/2006 | Mehl |
| 2006/0210945 A1 | 9/2006 | Savic et al. |
| 2006/0286507 A1 | 12/2006 | Dequeker |
| 2007/0154868 A1 | 7/2007 | Scharlack et al. |
| 2007/0231774 A1 * | 10/2007 | Massad .......................... 433/213 |
| 2008/0085489 A1 * | 4/2008 | Schmitt ........................... 433/75 |
| 2008/0090207 A1 | 4/2008 | Rubbert |
| 2008/0127698 A1 | 6/2008 | Luckey et al. |
| 2008/0206710 A1 | 8/2008 | Kruth et al. |
| 2008/0206714 A1 | 8/2008 | Schmitt |
| 2008/0209974 A1 | 9/2008 | Ewolski et al. |
| 2008/0300716 A1 | 12/2008 | Kopelman |
| 2009/0148813 A1 * | 6/2009 | Sun et al. ................... 433/201.1 |
| 2009/0162813 A1 | 6/2009 | Glor |
| 2009/0287332 A1 | 11/2009 | Adusumilli et al. |
| 2009/0291407 A1 | 11/2009 | Kuo |
| 2009/0325125 A1 | 12/2009 | Diangelo et al. |
| 2010/0015572 A1 | 1/2010 | Dierkes et al. |
| 2010/0062394 A1 | 3/2010 | Jones et al. |
| 2010/0086186 A1 | 4/2010 | Zug et al. |
| 2010/0094446 A1 | 4/2010 | Baloch et al. |
| 2010/0105011 A1 | 4/2010 | Karkar et al. |
| 2010/0324875 A1 | 12/2010 | Kalili |
| 2011/0045442 A1 | 2/2011 | Adusimilli |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Hilsen et al. |
| 2012/0058449 A1 | 3/2012 | Sklarski et al. |
| 2012/0095732 A1 | 4/2012 | Fisker et al. |
| 2012/0100500 A1 | 4/2012 | Gao |
| 2012/0178045 A1 | 7/2012 | Massad |
| 2012/0179281 A1 | 7/2012 | Steingart et al. |
| 2012/0258426 A1 | 10/2012 | Boe |
| 2012/0285019 A1 | 11/2012 | Schechner et al. |
| 2012/0329008 A1 | 12/2012 | Fishman et al. |
| 2013/0108988 A1 | 5/2013 | Simoncic |
| 2013/0216978 A1 | 8/2013 | Thompson et al. |
| 2013/0218532 A1 | 8/2013 | Thompson et al. |
| 2013/0221554 A1 | 8/2013 | Jung et al. |
| 2013/0249132 A1 | 9/2013 | Thompson |
| 2013/0280672 A1 | 10/2013 | Thompson |
| 2013/0316302 A1 | 11/2013 | Fisker |
| 2014/0045967 A1 | 2/2014 | Thomas et al. |
| 2014/0272796 A1 | 9/2014 | Grobbee et al. |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0134094 A1 | 5/2015 | Thompson et al. |
| 2015/0230891 A1 | 8/2015 | Grobbee et al. |
| 2015/0245891 A1 | 9/2015 | Grobbee |
| 2015/0245892 A1 | 9/2015 | Grobbee |

(56) References Cited

U.S. PATENT DOCUMENTS

FOREIGN PATENT DOCUMENTS

| WO | WO-0132096 A2 * | 5/2001 | ............ A61C 19/04 |
| WO | 2009105661 | 8/2009 | |
| WO | 2009105700 | 8/2009 | |
| WO | 2010022479 | 3/2010 | |
| WO | WO 2010058822 A1 * | 5/2010 | |
| WO | 2012041329 | 4/2012 | |
| WO | 2012061652 | 5/2012 | |
| WO | 2012061655 | 5/2012 | |
| WO | 2012061659 | 5/2012 | |
| WO | 2012061660 | 5/2012 | |
| WO | 2014130536 | 8/2014 | |
| WO | 2015031062 | 3/2015 | |

OTHER PUBLICATIONS

PCT; International Search Report and Written Opinion dated Jul. 18, 2012 in Application No. PCT/US2011/059230.

PCT; International Preliminary Report on Patentability dated May 8, 2013 in Application No. PCT/US2011/059230.

PCT; International Search Report and Written Opinion dated Jul. 18, 2012 in Application No. PCT/US2011/059235.

PCT; International Preliminary Report on Patentability dated May 8, 2013 in Application No. PCT/US2011/059235.

PCT; International Search Report and Written Opinion dated Jul. 9, 2012 in Application No. PCT/US2011/059239.

PCT; International Preliminary Report on Patentability dated May 8, 2013 in Application No. PCT/US2011/059239.

PCT; International Search Report and Written Opinion dated Jul. 18, 2012 in Application No. PCT/US2011/059240.

PCT; International Preliminary Report on Patentability dated May 8, 2013 in Application No. PCT/US2011/059240.

USPTO; Final Office Action dated Mar. 6, 2014 in U.S. Appl. No. 13/249,2100.

EPO; European Search Report dated Mar. 4, 2014 in Application No. 11838839.6.

PCT; International Search Report and Written Opinion dated Jul. 25, 2014 in Application No. PCT/US2014/017136.

USPTO; Non-Final Office Action dated Oct. 23, 2014 in U.S. Appl. No. 13/823,621.

USPTO; Final Office Action dated dated Nov. 7, 2014 in U.S. Appl. No. 13/830,963.

USPTO; Restriction Requirement dated Sep. 5, 2014 in U.S. Appl. No. 13/823,621.

USPTO; Office Action dated Aug. 21, 2014 in U.S. Appl. No. 14/195,348.

USPTO; Final Office Action dated Oct. 21, 2014 in U.S. Appl. No. 14/195,348.

PCT; International Search Report and Written Opinion dated Aug. 7, 2014 in Application No. PCT/US2014/023654.

USPTO; Office Action dated Jan. 5, 2015 in U.S. Appl. No. 12/939,136.

USPTO; Non-Final Office Action dated Dec. 19, 2014 in U.S. Appl. No. 14/013,295.

USPTO; Restriction Requirement dated Feb. 12, 2015 in U.S. Appl. No. 13/369,238.

USPTO; Advisory Action dated Feb. 23, 2015 in U.S. Appl. No. 13/830,963.

USPTO; Notice of Allowance dated Jun. 6, 2014 in U.S. Appl. No. 13/249,210.

USPTO; Non-Final Office Action dated Jun. 20, 2014 in U.S. Appl. No. 13/830,963.

USPTO; Restriction Requirement dated Jul. 2, 2014 in U.S. Appl. No. 14/195,348.

EPO; European Search Report and Opinion dated Mar. 3, 2014 in Application No. 11838843.8.

USPTO; Final Office Action dated Sep. 25, 2015 in U.S. Appl. No. 12/939,136.

USPTO; Final Office Action dated Aug. 19, 2015 in U.S. Appl. No. 12/939,138.

USPTO; Non-Final Office Action dated Sep. 21, 2015 in U.S. Appl. No. 13/369,238.

USPTO; Notice of Allowance dated Aug. 24, 2015 in U.S. Appl. No. 13/823,662.

USPTO; Non-Final Office Action dated Aug. 13, 2015 in U.S. Appl. No. 13/830,963.

USPTO; Non-Final Office Action dated Aug. 11, 2015 in U.S. Appl. No. 14/195,348.

U.S. Non-Final Office Action dated Apr. 9, 2015 in U.S. Appl. No. 12/939,138.

U.S. Notice of Allowance dated Jun. 22, 2015 in U.S. Appl. No. 13/823,621.

U.S. Notice of Allowance dated Apr. 13, 2015 in U.S. Appl. No. 14/013,295.

* cited by examiner

SYSTEM AND PROCESS FOR DUPLICATION OF DENTURES

FIELD OF THE INVENTION

The present invention relates to the field of denture manufacture and particularly the duplication of existing dentures.

BACKGROUND

Dentures are worn by a considerable number of individuals. The average life span of a denture is approximately seven years, although many individuals continue to wear dentures well beyond that time period. Additionally, dentures become ill-fitting over time due to changes in the patients anatomy. Dentures may also become damaged over time as well. Also, some individuals may want to have a spare denture in case of the loss of the original denture or in the event of an accidental fracture of their primary denture. The cost and time of creating a new denture can often be considerable. Thus, it is often desirable to make a new denture based on an existing denture, particularly if the patient is satisfied with their existing dentures.

The duplication of an existing denture is preferable in most circumstances as the transfer of the shape of the existing dentures maintain the neuromuscular control to the new dentures. Minor modifications are often necessary as well to compensate for worn teeth and denture bases and for changes in the patients anatomy.

There are a number of techniques currently available for providing a patient with a duplicate denture. Many times a temporary denture will be fabricated by the dentist for the patient while the new denture is being fabricated. However, these temporary dentures are usually ill-fitting, uncomfortable and not intended for continued use. Duplicate dentures are normally fabricated based on the prescription and information from the individual's original dentures, if available. Often, there may be a considerable amount of time that has elapsed and such information may not be available. So rather than create a new denture from scratch, it is often more sensible to duplicate a new denture from existing dentures.

There are a number of techniques currently available for duplicating existing dentures. These techniques involve producing a mold by inserting the existing denture into a rigid container such as a duplicating flask, dental flask or other container filled with an elastic material such as alginate or silicon putty. A wax or auto-polymerizing resin template is then fabricated from the mold. This template is tried in the patient's mouth and modifications are made if necessary. Then the final denture is made and provided to the patient. Other variations include forming a wax rim instead of the auto-polymerizing resin or using a silicon putty to create the denture base. These techniques require several try-ins to ensure the proper fit in the patient and the creation of initial templates or wax rims, then the actual denture. This entails considerable time and expense for the patient.

SUMMARY OF THE INVENTION

The present invention provides systems and processes for the precise duplication of dentures from existing dentures. The duplicate dentures can be ready for delivery to the patient in a relatively short time frame. The duplicate denture may even be manufactured in the dentist office.

A preferred embodiment of the present invention provides systems and processes for duplicating a denture from an existing denture. The denture is scanned and the scanned images are used to create a fully digitized denture. A denture base can be fabricated from this model and denture teeth can be designed or selected from a library that is the closest fit to the original denture. The teeth in the digital model are offset a preset distance. The teeth with offset are then subtracted from the digitized denture. The margins of the denture are then cleaned after subtracting the teeth. The denture base is then ready for manufacturing. The teeth are then installed onto the denture base.

In an alternative embodiment of the present invention, the interior and exterior of the dentures can be scanned as discussed above. The dentist can also provide additional information regarding the dentures and the patient as well to ensure a proper fit. This additional information may be used to change the digitized model of the denture.

Another embodiment of the present invention may use the existing dentures to create bite impressions which are scanned along with the existing dentures. These scans are used to create a digital three dimensional image of the denture. This digital model is then used to fabricate a duplicate denture.

The digitized denture model in another preferred embodiment, may also be used to create a denture base. The teeth are subtracted from the model, and teeth are either selected from a library or the teeth may be directly fabricated from the denture information. The denture teeth are temporarily installed in the denture base. This temporary denture is then tried onto the patient. If the fit is not correct, then the denture is used as a secondary impression tray to create a set of bite impressions. These impressions are scanned and used to select or fabricate another denture base. The teeth are installed again and the denture is tried on the patient. This process is repeated until the patient is satisfied. At that point, the teeth are permanently installed, the denture is finally processed and delivered to the patient.

A preferred embodiment of the present invention creates a best fit for the duplicate denture that maintains the occlusal scheme of the existing denture. The occlusal scheme is maintained while allowing changes to the denture for anatomical, functional and aesthetic reasons.

The term anatomical landmarks refers to the structures on the anatomy of the wearer that define the periphery of the denture. Examples of anatomical landmarks include at least one of a vertical height relation to an upper and lower bite alignment, a lip support, a smile line, a centric relationship and a midline measurement.

These and other features of the claimed inventions will be evident from the ensuing detailed description of preferred embodiments, from the drawings and from the claims.

DETAILED DESCRIPTION

The present invention provides systems and process for the duplication of dentures. Descriptive embodiments are provided before for explanatory purposes. It is to be expressly understood that the present invention is not be limited to these descriptive embodiments. Other embodiments are considered to be within the scope of the present invention, including without limitation the use of the present invention for other applications, such as denture duplication, dental implants, and other dental and orthodontic applications. The descriptions below discuss the systems of the present invention as used in dental labs, but it is to be expressly understood that these systems could also be implemented in the dentist office or through a network allowing interaction between the dentist and the dental lab through the systems. The processes and systems of the present invention may also be used in combination with all or parts of the following applications, entitled System and Processes for Optimization for Dentures, Ser. No. 12/939,141; System and Process for Forming Anatomical Features in Dentures, Ser. No. 12/939,138; and Removable Handle for Use with Dentures, Ser. No. 12/939,143 all of which are hereby incorporated herein by reference.

The terms denture base generally refers to the part of a denture that fits the oral mucosa of the basal seat, restores the normal contours of the soft tissues of the edentulous or partly edentures mouth, and supports the artificial teeth. The term denture refers to the denture base with the artificial teeth attached.

Overview

A preferred embodiment of the present invention provides systems and processes for duplicating a denture from an existing denture. The denture is scanned and a best fit procedure is used to create a fully digitized denture. An offset is added to the overall dimension of the denture teeth. The denture teeth with the offset are then subtracted from the digitized denture model. The margins of the denture are then cleaned after subtracting the teeth. The denture base is then ready for manufacturing. The teeth are then installed onto the denture base.

Process

Figure 1:
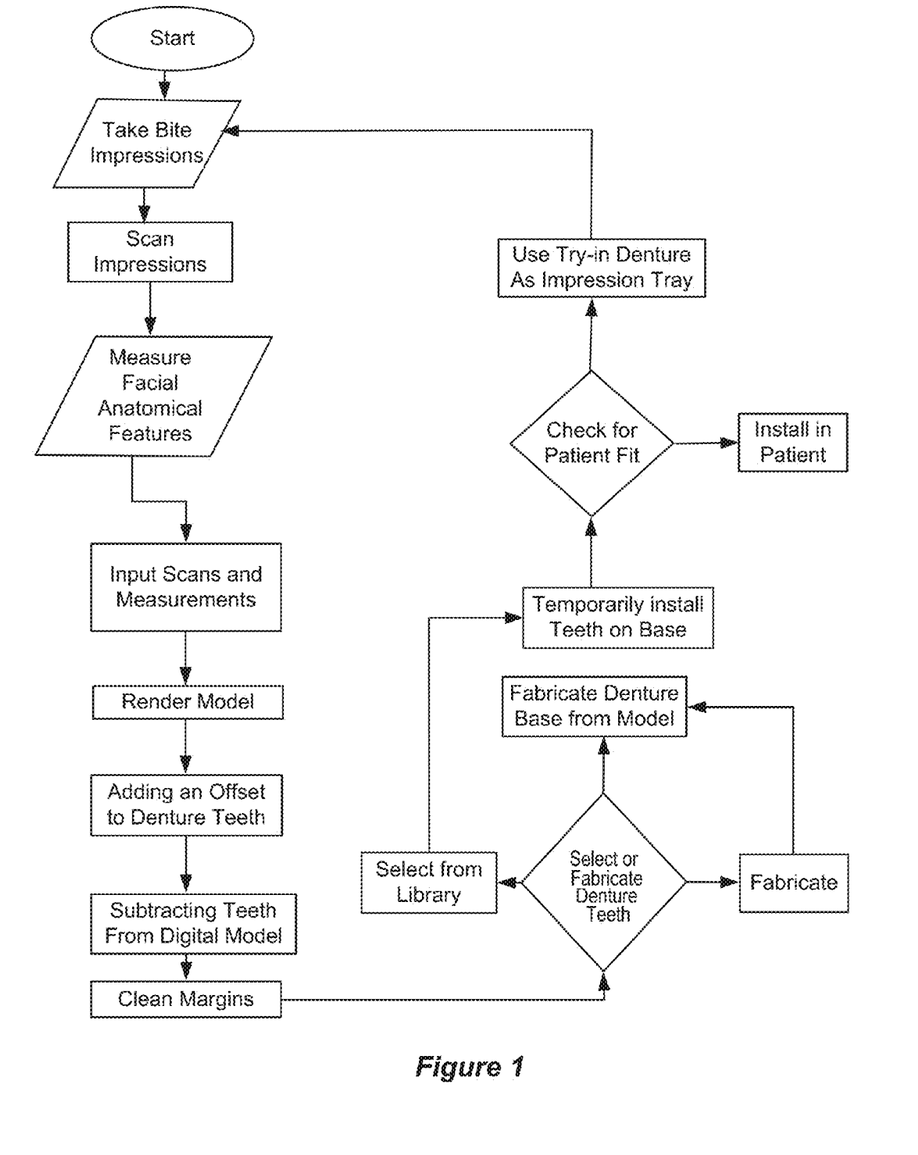
FIG. 1 is a diagram of the work flow process of one preferred embodiment.
Figure 2:
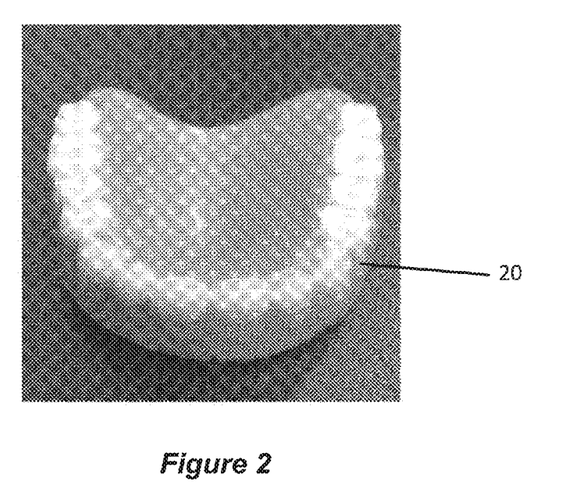
FIG. 2 is an illustration of a denture to be duplicated.
Figure 3:
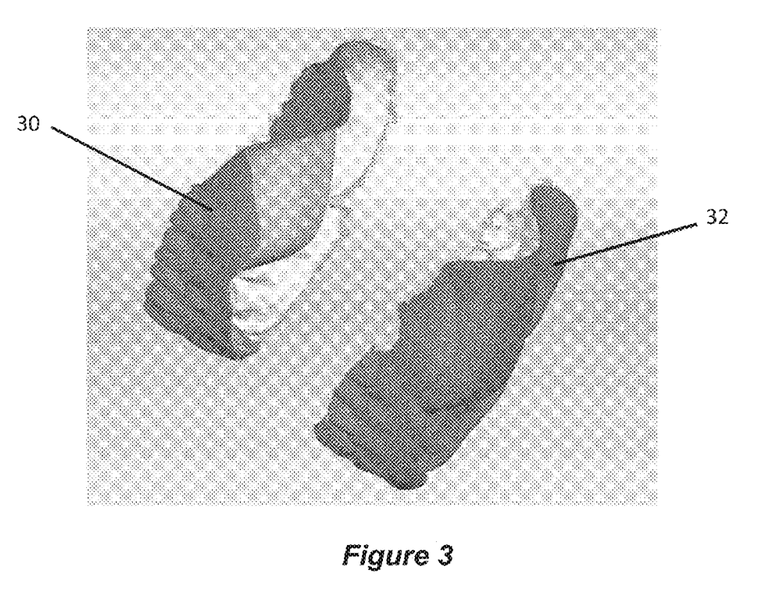
FIG. 3 is an illustration of the scanned images of the denture.
Figure 4:
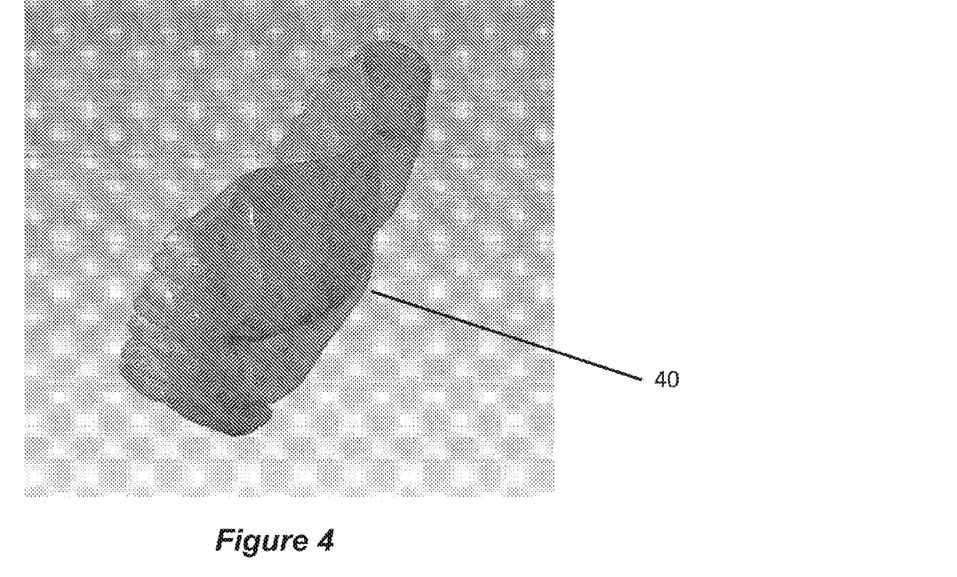
FIG. 4 is an illustration of a digital three dimensional model of the denture.
Figure 5:
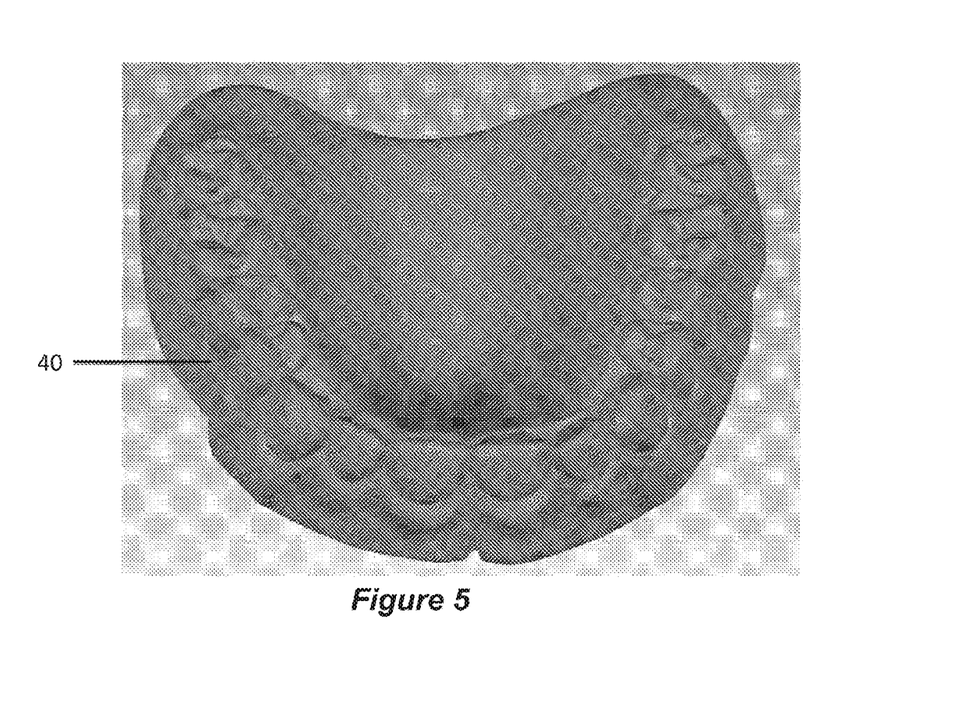
FIG. 5 is another view of the digital model of the denture.

A preferred embodiment of the present invention is disclosed that allows new dentures to be created from an existing denture. The patient provides their existing dentures to the dentist for scanning. Digital scans 30, 32 are created from the inside and outside of the original denture 20 as shown in FIGS. 2 and 3. Once the scans are performed, the denture can be returned to the patient. The system, as shown in the work flow diagram of FIG. 1, applies a series of routines to create a digital three dimensional model 40 of the existing denture as shown in FIGS. 4 and 5.

Figure 6:
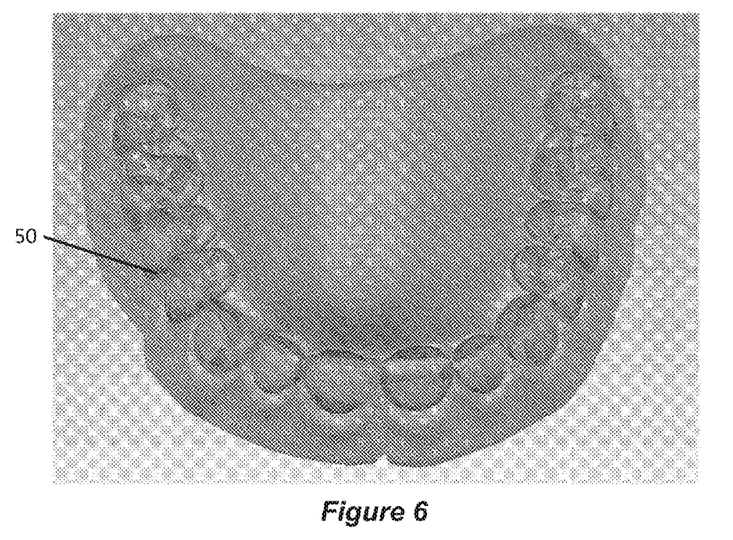
FIG. 6 is an illustration of the digital denture model.
Figure 7:
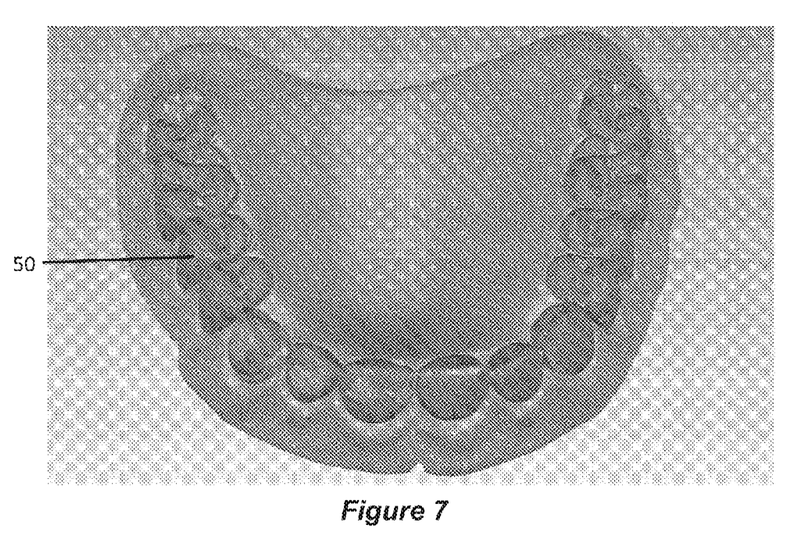
FIG. 7 is an illustration of the model with an offset added to the teeth.
Figure 8:
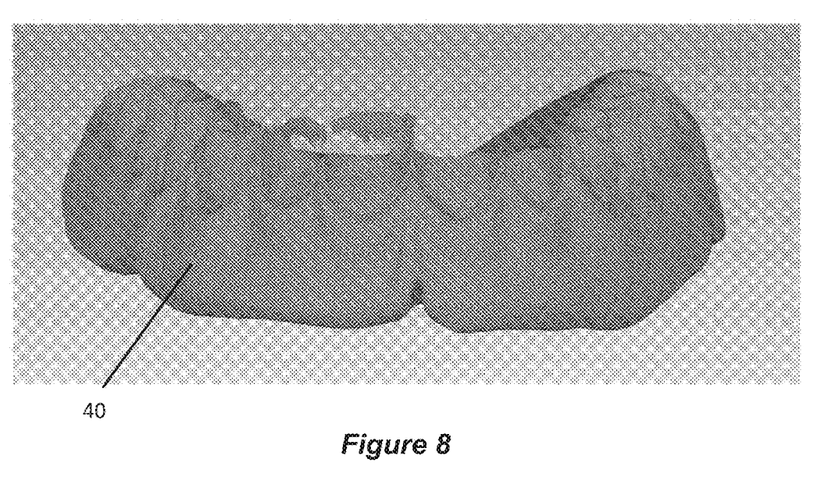
FIG. 8 is an illustration of the digital denture with the teeth being subtracted.
Figure 9:
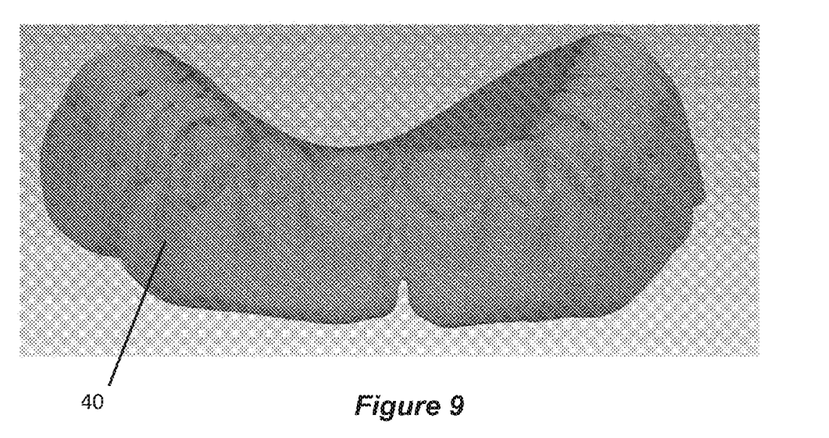
FIG. 9 is an illustration of the digital denture base being cleaned after the teeth has been subtracted.
Figure 10:
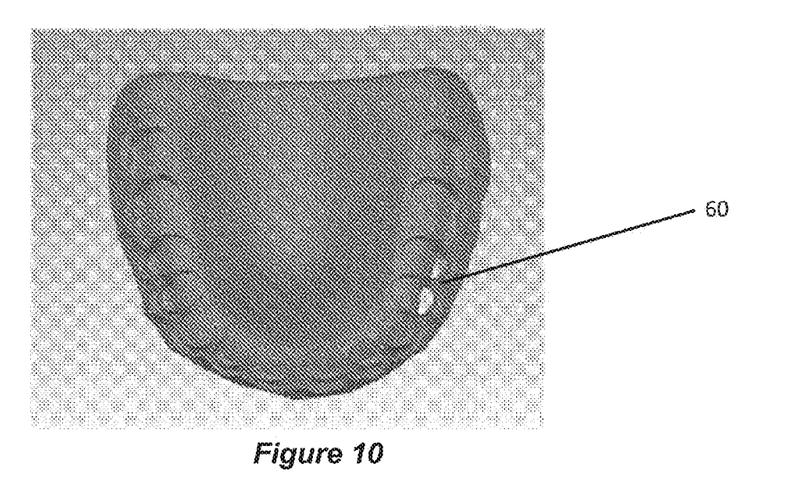
FIG. 10 is an illustration of the machined denture base.

This digitized denture model 40 is then digitally compared with denture teeth from a library to select the best fitting denture teeth 50 in the scanned model as shown in FIG. 6. The denture teeth 50 are then offset by a preset amount as shown in FIG. 7. This adds an overall thickness to the teeth. The teeth are then digitally subtracted from the digitized denture model as shown in FIG. 8. The offset added to the teeth creates slightly larger pockets in the denture base. The margins are then cleaned after the teeth have been subtracted as shown in FIG. 9. This creates a digital model 60 of the denture base for the patient as shown in FIG. 10.

Figure 11:
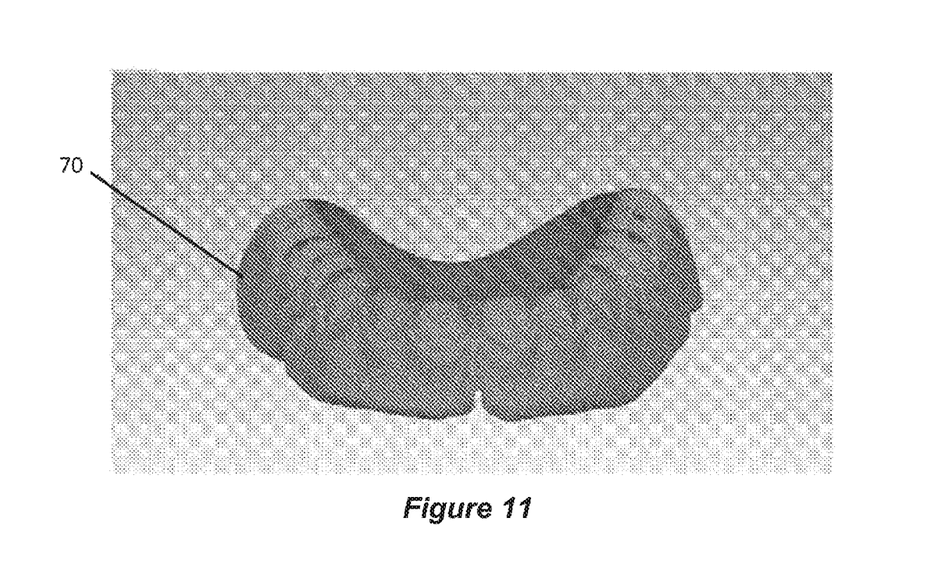
FIG. 11 is another view of the machined denture base.
Figure 12:
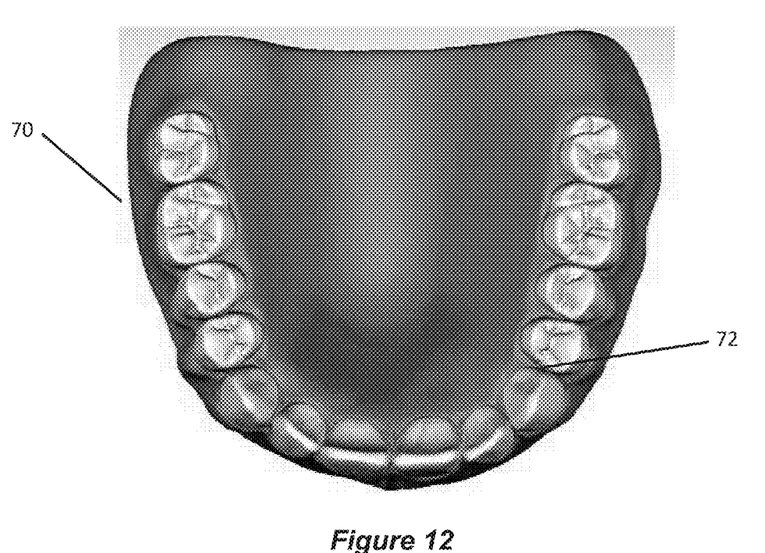
FIG. 12 is a view of the duplicated denture.
Figure 13:
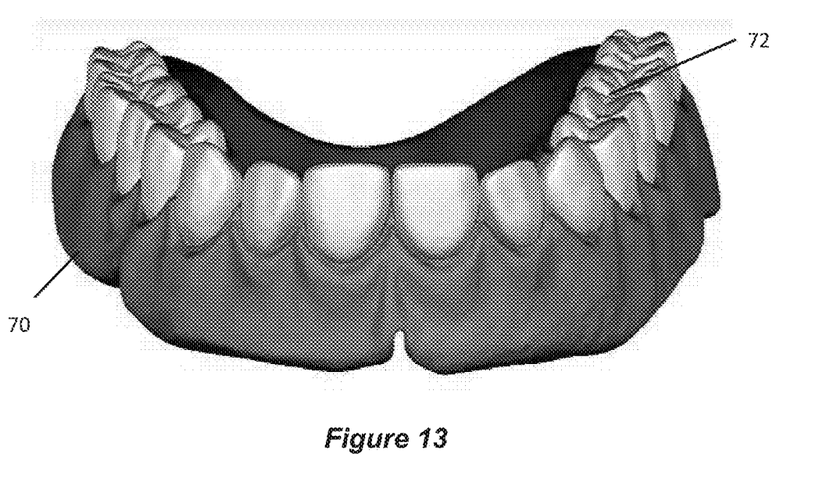
FIG. 13 is another view of the duplicated denture.

The denture teeth may be either selected from a library or fabricated from the digital model in a number of process. In this preferred embodiment, the denture base is machined in acrylic based on the digital model 60. This can be done relatively quickly. Once the denture base 70 has been fabricated as shown in FIGS. 10 and 11, the teeth 72 are installed and delivered to the patient for try-in and use as shown in FIGS. 12 and 13.

This entire process can be done in a relatively fast time frame. In some instance, the duplication process can take place in the dentist offices. In other instances, the scanned images of the existing denture can be transmitted to a nearby dental lab where the denture is fabricated and courier to the dentist.

In an alternative embodiment of the present invention, the interior and exterior of the dentures can be scanned as discussed above. The dentist can also provide additional information regarding the dentures and the patient as well. For example, the dentist may notice that the dentures are no longer properly fitting due to wear of the denture base or the teeth or due to changes in the patient's anatomy. This additional information may be used to change the digitized model of the denture.

In yet another alternative embodiment of the present invention, the dentist may provide additional information beyond the scanned images of the interior and exterior of the dentures. The dentist may use those existing dentures as an impression tray to take bite impressions of the patient. Those bite impressions are then scanned and used along with the scanned images of the interior and exterior of the dentures to create the digitized denture.

The occlusal scheme of the existing denture is maintained in the duplicate denture. The duplicate denture can be modified to accommodate anatomical, aesthetic and functional changes that might be necessary.

The digitized denture model 40, in another preferred embodiment, may also be used to create a model for a denture base. The teeth are subtracted from the model, and a denture base is directly fabricated from the denture base information. A denture base is then fabricated, the margins are cleaned and teeth are temporarily installed. This try-in denture is then tried onto the patient. If the fit is not correct, then the denture is used as a secondary impression tray to create a set of bite impressions. These impressions are scanned and used to select or fabricate another denture base. The teeth are installed again and the denture is tried on the patient. This process is repeated until the patient is satisfied. At that point, the teeth are permanently installed, the denture is finally processed and installed to the patient.

A preferred embodiment of the present invention may be implemented in a number of ways.

The above descriptions are intended for explanatory purposes and are not meant to the limit the scope of the claimed inventions. Other embodiments may be covered under the claims as well.

What is claimed is:

1. A computer implemented method for duplicating dentures from an existing denture, the method comprising the steps of:

taking a scan of the existing denture comprising existing teeth and an existing denture base;

creating a digital three dimensional model comprising digital scanned teeth and a digital scanned denture base from the scan of the existing denture, wherein the creating comprises:
  fitting digital denture teeth from a library to a digital denture in response to the digital three dimensional model;
  offsetting the digital scanned teeth by a predetermined amount to create offset digital denture teeth, wherein the offsetting comprises:
    selecting denture teeth that are a closest fit to the existing teeth from among the library;
    adding a thickness to the digital scanned teeth in response to the selecting, the thickness comprising the predetermined amount;
  subtracting the offset digital denture teeth from the digital scanned denture base to create pockets in the digital scanned denture base, said pockets being larger than the digital denture teeth prior to the step of offsetting the digital scanned teeth;
  removing margins from the digital denture;
manufacturing a first denture base from the digital three dimensional model, wherein the manufacturing comprises fabricating pockets in the first denture base corresponding to the offset digital denture teeth in response to the digital three dimensional model; and
installing teeth corresponding to the digital denture teeth to the first denture base.

2. The method of claim 1, wherein the step of removing the margins comprises cleaning digital artifacts from the digital denture.

3. The method of claim 1 wherein the step of taking the scan of the existing denture includes:
  taking a scan of the interior of the existing denture; and
  taking a scan of the exterior of the existing denture; and
  merging the scans together to form one model.

4. The method of claim 1 wherein the method further includes:
  providing additional information to correct the fit of the existing denture to improve the fit of the duplicate denture.

5. The method of claim 1 wherein the method further includes:
  using the existing denture as an impression tray;
  taking bite impressions using the existing denture;
  scanning the bite impressions; and
  creating a digital model of the existing denture in response to the bite impressions.

6. The method of claim 1 further comprising:
  receiving try-in fitting data collected by try-in fitting the first denture base in a patient's mouth;
  manufacturing a second denture base based on the digital three dimensional model and the try-in fitting data.

7. The method of claim 4 wherein said method further includes adjusting the digital three dimensional model according to measurements of facial anatomical landmarks of a patient, the anatomical landmarks correlating to the periphery of the existing denture comprising at least one of a vertical height relation to an upper and lower bite alignment, a lip support, a smile line, a centric relationship, and a midline measurement.

8. The method of claim 1 wherein the method further includes adjusting the digital three dimensional model according to measurements of facial anatomical landmarks.

9. A computer implemented method for duplicating dentures from an existing denture comprising the steps of:
  receiving patient data comprising a scan of an existing denture comprising existing teeth and an existing denture base;
  creating a digital three dimensional model comprising digital scanned teeth and a digital scanned denture base from the patient data,
    wherein the creating of the digital three dimensional model comprises:
      fitting digital denture teeth from a library to a digital denture base in response to the digital three dimensional model;
      offsetting the digital scanned teeth by a predetermined amount to create offset digital denture teeth, wherein the offsetting comprises:
        selecting denture teeth that are a closest fit to the existing teeth from among the library;
        adding a thickness to the digital scanned teeth in response to the selecting, the thickness comprising the predetermined amount;
      subtracting the offset digital denture teeth from the digital scanned denture base to create pockets in the digital scanned denture base, said pockets being larger than the digital denture teeth prior to the step of offsetting the digital scanned teeth
      removing margins from the digital denture base
  manufacturing a first denture base based on the digital three dimensional model; and
  installing teeth corresponding to the digital denture teeth to the first denture base.

10. The method of claim 9 wherein the patient data comprises bite impression data.

11. The method of claim 9 wherein the patient data comprises measurements of facial anatomical landmarks of a patient, the anatomical landmarks correlating to the periphery of the existing denture.

12. The method of claim 9 wherein the patient data comprises:
  bite impression data; and
  measurements of facial anatomical landmarks.

13. The method of claim 9 further comprising:
  receiving try-in fitting data collected by try-in fitting the first denture base in a patient's mouth wherein the first denture base comprises a try-in denture base;
  manufacturing a second denture base based on the digital three dimensional model and the try-in fitting data wherein the second denture base comprises a permanent denture base.

14. The method of claim 9 wherein the patient data comprises try-in fitting data.

15. The method of claim 9 wherein the step of installing teeth corresponding to the digital denture teeth to the first denture base comprises: fabricating the teeth corresponding to the digital denture teeth from the library in response to the digital three dimensional model, or fabricating the teeth based on the digital scanned teeth.

16. The method of claim 9 wherein the step of manufacturing the first denture base comprises:
  fabricating pockets in the first denture base corresponding to the offset digital denture teeth in response to the digital three dimensional model.

17. The method of claim 1 wherein the step of installing teeth corresponding to the digital denture teeth to the first denture base comprises: fabricating the teeth corresponding to the digital denture teeth from the library in response to the digital three dimensional model, or fabricating the teeth based on the digital scanned teeth.

* * * * *